United States Patent
Kodadek et al.

(10) Patent No.: US 6,613,582 B1
(45) Date of Patent: Sep. 2, 2003

(54) METHODS FOR RAPID AND EFFICIENT PROTEIN CROSS-LINKING

(75) Inventors: Thomas J. Kodadek, Dallas, TX (US); David A. Fancy, Dallas, TX (US); Stephen A. Johnston, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/578,950

(22) Filed: May 25, 2000

Related U.S. Application Data

(60) Provisional application No. 60/135,766, filed on May 25, 1999.

(51) Int. Cl.[7] .................. G01N 33/53; G01N 33/543
(52) U.S. Cl. .................. 436/524; 435/4; 435/6; 435/7.1; 435/7.9; 435/7.92; 435/174; 435/175; 435/176; 435/177; 435/961; 435/964; 435/971; 436/73; 436/84; 436/164; 436/172; 436/518; 436/519; 436/523; 436/525; 436/526; 436/528; 436/536; 436/805; 436/806; 436/823; 436/824; 436/905

(58) Field of Search .................. 435/4, 7.1, 7.92, 435/174–176, 6, 7.9, 177, 961, 964, 971; 436/518, 164, 172, 73, 805, 824, 84, 519, 523, 524, 525, 526, 528, 536, 806, 823, 905

(56) References Cited

U.S. PATENT DOCUMENTS

| | | | |
|---|---|---|---|
| 5,564,419 A | | 10/1996 | Lundsgaard et al. ........ 128/633 |
| 5,744,302 A | * | 4/1998 | Sessler et al. ................. 435/6 |
| 5,877,230 A | * | 3/1999 | Kutal ........................ 522/148 |
| 6,063,637 A | * | 5/2000 | Arnold et al. ............ 422/82.01 |
| 6,187,532 B1 | * | 2/2001 | Wood et al. .................... 435/6 |
| 6,406,850 B2 | * | 6/2002 | Volkers et al. ................. 435/6 |

OTHER PUBLICATIONS

Campbell et al. Protein cross–linking mediated by metalloporphyrins. Bioorganic and Medicinal Chemistry. (1998) vol. 6, No. 8, pp. 1301–1307.*

Muheim et al. Ruthenium–mediated protein cross–linking and stabilisation. J. Am. Chem. Soc. (1993) vol. 115, No. 12, pp. 5312–5313.*

Kamps–Hotzapple et al. Effect of encapsulated ammonium persulfate on DNA binding in sequencing gels. BioTechniques. (1995) vol. 18, No. 6, pp. 1006–1007.*

Bertrand et al., "Probing the hydrophobic interactions in the skeletal actomyosin subfragment 1 and its nucleotide complexes by zero–length cross–linking with a nickel–peptide chelate," *Biochemistry*, 36:9703–9714, 1997.

Browns et al., "Highly specific oxidative cross–linking of proteins mediated by a nickel–peptide complex," *Biochemistry*, 34:4733–4739, 1995.

Chen et al., "Identification of the target of a transcription activator protein by protein–protein photocrosslinking," *Science*, 265:90–92, 1994.

(List continued on next page.)

*Primary Examiner*—Long V. Le
*Assistant Examiner*—Kartic Padmanabhan
(74) *Attorney, Agent, or Firm*—Fulbright & Jaworski

(57) ABSTRACT

The present application describes novel uses of ruthenium bipyridyls or palladium porphyrins as photo-activatable crosslinking agents. Crosslinking can be between any two molecules including peptides, proteins, or compounds. Crosslinking occurs in the presence of an electron donor such as ammonium persulfate, and requires only moderate intensity visible light. Crosslinking can be between peptides, polypeptides or lead candidate compounds to unknown target molecules. Reagents utilyzing ruthenium bipyridyls and palladium porphyrins crosslinkers for use in diagnostic and detection scenarios are also disclosed.

14 Claims, 7 Drawing Sheets

OTHER PUBLICATIONS

Dorman and Prestwich, "Benzophenone photophores in biochemistry," *Biochemistry* 33:5661–5673, 1994.

Fancy and Kodadek, "Chemistry for the analysis of protein–protein interactions: rapid and efficient cross–linking triggered by long wavelentgh light," *Proc. Natl. Acad. Sci. USA*, 96:6020–6024, 1999.

Fancy and Kodadek, "Site–directed oxidative protein crosslinking," *Tetrahedron*, 53:11953–11960, 1997.

Fancy et al., "Scope, limitations and mechanistic aspects of the photo–induced cross–linking of proteins by water–soluble metal complexes," *Chem Bio*, 7:697–708, 2000.

Friedrichson and Kurzchalia, "Microdomains of GPI–anchored proteins in living cells revealed by crosslinking," *Nature*, 394:802–805, 1998.

Grimshaw et al., "Development of an equilibrium immunoassay using electrochemiluminescent detection for a novel recombinant protein product and its application to pre–clinical product development," *J. Pharm. Biomed. Anal.* 16:605–612, 1997.

Kopp et al., "Subunit arrangement in the human 20S proteasome," *Proc. Natl. Acad. Sci. USA*, 94:2939–2944, 1997.

Nickel et al., "Mechanism and kinetics of the photocatalyzed oxidation of p–phenylenediamines by peroxydisulfate in the presence of tri–2,2'–bipyridylylruthenium (II)," *J. Phys. Chem.*, 98:2883–2888, 1994.

Norcum and Warrington, "Structural analysis of the multienzyme aminoacyl–trna synthetase complex: a three–domain model based on reersible chemical crosslinking," *Prot. Sci.*, 7:79–87, 1998.

Verweij et al., "Photodynamic protein cross–linking," *Biochemica et Biophysica Acta*, 647:87–94.

Woltman et al., "Chromatographic detection using tris (2,2'–bipyridyl)ruthenium (III) as a fluorogenic electron–transfer reagent," *Anal. Chem.* 71:1504–12, 1999.

Xie et al., "Biochemical characterization of the TATA–binding protein–Gal4 activation domain complex," *J Biol Chem*, 275:31914–31920, 2000.

\* cited by examiner

− + + [Ru(bpy)$_3$]$^{2+}$/hv/S$_2$O$_8$$^{2-}$
− − + Histidine

● − (Gal80/H$_6$-AAD)$_4$

● − (Gal80/H$_6$-AAD)$_2$
● − (Gal80)$_2$/H$_6$-AAD

● − Gal80/H$_6$-AAD

− $^{32}$P-AAD

METHODS FOR RAPID AND EFFICIENT PROTEIN CROSS-LINKING

This application claims priority to U.S. Provisional application Ser. No. 60/135,766, filed May 25, 1999.

The government may own rights in the present invention pursuant to grant number GM-58175 from the National Institutes of Health.

BACKGROUND OF THE INVENTION

1. Field of the Invention

The present invention relates generally to the fields of biochemistry and cell biology. More particularly, it concerns novel cross-linking reagents for use in identifying molecular interactions and linking known molecules.

2. Description of Related Art

Large, multi-protein complexes mediate most important biological processes. A central question in the study of these "protein machines" (Alberts, 1998) is to elucidate the lacework of protein-protein interactions and, ideally, to ascertain how this architecture might change during the course of the catalytic cycle in question. Chemical cross-linking (Mattson et al., 1993; Ji and Ji, 1989; Gaffnley, 1985) is a potentially useful technique for this purpose. However, cross-linkers are most often applied to the analysis of interactions between a few proteins (Bertrand et al., 1997; Jiang et al., 1993; Jiang and Kodadek, 1993), while successful analysis of contacts in large complexes is more difficult (Friedrichson and Kurzchalia, 1998; Schere and Krieg, 1991; Norcum and Warrington, 1998). This is largely due to the fact typical bifunctional cross-linkers, comprised of two electrophiles connected by a linker arm, have many drawbacks with regard to complex systems. For example,they are constitutively reactive and cannot be "triggered" at a desired time. Also, poor yields are often obtained even with long incubation times. Even more seriously, large-scale modification of nucleophilic side chains, such as the acylation of lysines, on the surface of the proteins during the extended incubation times required for typical reagents raises the concern of artifactual results due to structural destabilization.

Protein-protein interactions vary in their strength of association by several orders of magnitude. These associations can be so strong as to be functionally irreversible or weak enough as to allow only transient association between proteins. Weak interactions between proteins can often times play fundamental roles in biologic systems. However, understanding these interactions and dissecting the relevant proteins involved in the interactions is problematic. Trapping such proteins involved in weak interactions with chemical cross-linkers is a powerful way of identifying them.

Another instance where weak protein interactions are encountered is in obtaining probes or reagents that bind target proteins. Methodologies for generating peptides that bind a target are known. Antibody generation against a target has been one of the preferred methods for generating such high binding affinity probes, several novel approaches have become routine. These include systems for screening large numbers of peptides for binding including recombinant antibody generation, yeast two-hybrid systems, phage display and combinatorial libraries. Screens for binding can either be genetic or involve high throughput assays to isolate peptides or polypeptides with binding specificities for a target. One problem often seen with peptides or polypeptides is weak affinity for the target against which they are directed. Cross-linking reagents can be used to trap these weak interactions, turning a probe with modest affinity and limited utility into a more useful reagent.

A final scenario where crosslinkers can be used is in combination with known compounds, peptides or proteins to covalently trap these compounds in key molecular interactions. In this scenario, a known or candidate compound would be conjugated with a crosslinking agent prior to adding to a biologic system. Upon addition and binding to a target such as a receptor, enzyme, or any other target site, crosslinking would permanently attach the compound, peptide or protein to its target. This would be especially useful in vivo for increasing efficacy of pharinaceutical compositions.

There are many cross-linkers that have been characterized for defined purposes. Use of these cross-linkers is limited by many factors, including non-specific reactivity, constitutive reactivity, harsh chemical conditions necessary for reaction, destructive modifications of target enzymatic activity, and an inability to use the cross-linkers in complex biologic systems such as in whole cells or in vivo. Thus, there is a need for cross-linkers that do not suffer from these drawbacks.

SUMMARY OF THE INVENTION

The present invention describes methods of covalently bonding a first molecule to a second molecule in a controlled way. The method comprises bringing the two molecules in molecular proximity to each other, contacting the two molecules with a metal-ligand complex, and subjecting the complex to light which photoactivates the complex, resulting in bonding the first and second molecules mediated by the metal-ligand complex. In preferred embodiments, the first molecule is a protein, an antibody, drugs, or a peptide. The peptide may be conjugated to a metal. In other preferred embodiments, the second molecule is a protein.

The present invention describes complexes useful for bonding two molecules together that comprising a palladium (II) porphyrin or a Ru(II)(bypyridyl) used in combination with an electron acceptor. In preferred embodiments, the electron acceptor is ammonium persulfate. The complex may also comprises a detectable agent.

The light used to photoactivate the complex has a wavelength of greater than 380 nm but less than 800 nm. The intensity of the light used to photoactivate the complex is between 1 watt and 1000 watts for periods of time between 30 milliseconds to 30 seconds.

The present application also describes methods where the first and second molecules are located in a cell. The complex-linked molecules may be isolated allowing identification of the first and/or second molecule.

In other embodiments of the present invention, an alternative method of covalently bonding a first molecule to a second molecule is described. This involves initially forming a metal-ligand complex with a first molecule, then contacting this first molecule with a second molecule, subjecting the complex to light to photoactivate the complex, resulting in bonding of the first molecule to the second molecule. In preferred embodiments, the first molecule is a protein, an antibody, or a peptide. The peptide may be conjugated to a metal. In other preferred embodiments, the second molecule is a protein. In other embodiments, the second molecule is a drug.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
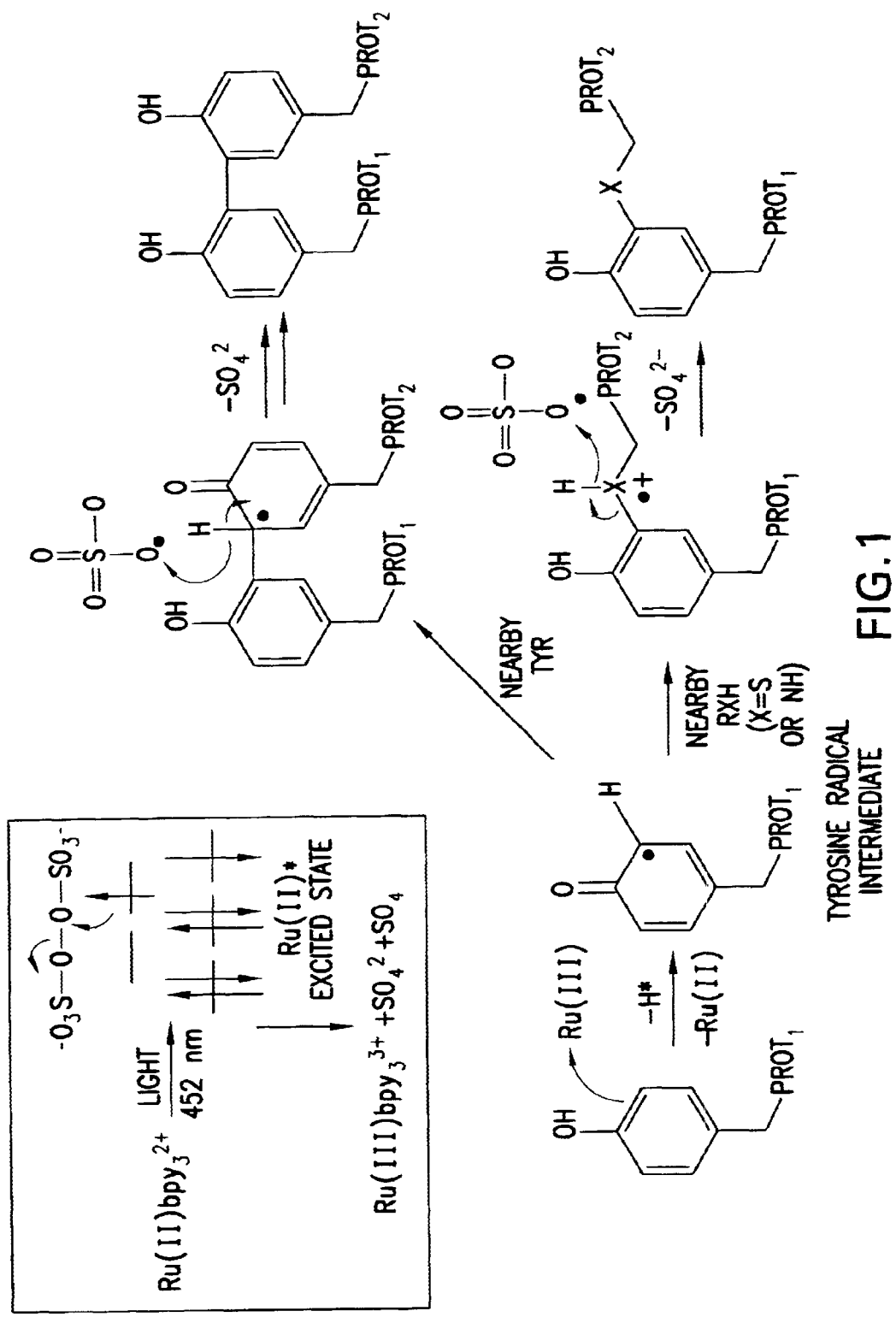
FIG. 1. Mechanism-based design of a photo-initiated protein cross-linking reaction. The boxed part of the figure represents schematically the electron flow when Ru(II) bpy$_3^{2+}$ is photolyzed in the presence of a persulfate, generating Ru(III) and sulfate radical. Two hypothetical mechanisms are shown by which these reactive intermediates could cross-link two associated proteins. The top pathway depicts formation of 2,2'-dityrosine-coupled adducts while the bottom pathway depicts a reaction between a tyrosyl radical and other nucleophilic side chains. This figure represents only a mechanistic hypothesis on which the reaction was designed. The true mechanism of Ru(II)byp$_3$+/persulfate-mediated cross-linking remains to be determined experimentally.

The present application describes novel use of photo-activatable crosslinking. agents. These agents are either ruthenium bipyridyls or palladium porphyrins, which have the ability to covalently crosslink two molecules that are in close proximity to each other. These two molecules can be peptides, proteins, or chemical compounds from a number of sources. Modest affinities between the two molecules can be trapped in a covalent structure upon light activation of the crosslinking agents. Efficient crosslinking occurs in the presence of an electron donor such as ammonium persulfate, and requires only moderate intensity visible light. The crosslinking agents are cell membrane permiable, allowing their use in whole cells or in vivo. The use of visible light rather than higher intensity UV light also makes these crosslinking methodologies very versatile in biologic systems. Molecules that have been crosslinked together can be isolated by a number of techniques and identified.

Other uses of the ruthenium bipyridyls and palladium porphyrins crosslinkers include crosslinking peptides, polypeptides or lead candidate compounds to unknown target molecules. These peptides, polypeptides or lead compounds can be derived from a number of possible sources, including but not limited to various genetic screens such as phage display of random peptides, yeast two hybrid systems, as well as combinatorial chemistry techniques and high throughput screening. Any candidate compound, peptide, or polypeptide can be initially complexed with the ruthenium bipyridyls or palladium porphyrins, and then mixed with test mixtures. Photoactivation can then crosslink the known candidate compound to potential target molecules. As in the case above, modest affinities between the candidate molecule and its target can be trapped in a covalent structure upon light activation of the crosslinking agents. Following crosslinking, complexes can be isolated and identified.

In addition to their utility as general crosslinking agents for identification and isolation of peptides, polypeptides or compounds, reagents utilyzing ruthenium bipyridyls and palladium porphyrins crosslinkers can be used in diagnostic and detection scenarios. These scenarios make use of peptides or compounds previously modified with the crosslinkers as probes that have affinities for defined target molecules. Techniques similar to various immunodetection techniques, including ELISA, Western blotting, immunohistochemistry, and FACS, can be adapted to these novel probes. Again, modest affinities between the probe and its target can be trapped in a covalent structure upon light activation of the crosslinking agents. Following crosslinking, complexes can be isolated, identified or quantitated.

1. Cross-Linking Reagents

Ruthenium bipyridyls and palladium porphyrins can be used as crosslinking agents as described in the present application. In general, both are bifunctional cross-linking reagents which serve to join a first material, i.e. a protein, with a second material, for example, an interacting protein. Both can also be used as heterobifunctional crosslinkers. Here a two-stage crosslinking process is performed where a material of interest, for example a peptide, polypeptide or compound, can be isolated, linked to one end of the reagent and then introduced for reaction at the other end.

Figure 7:
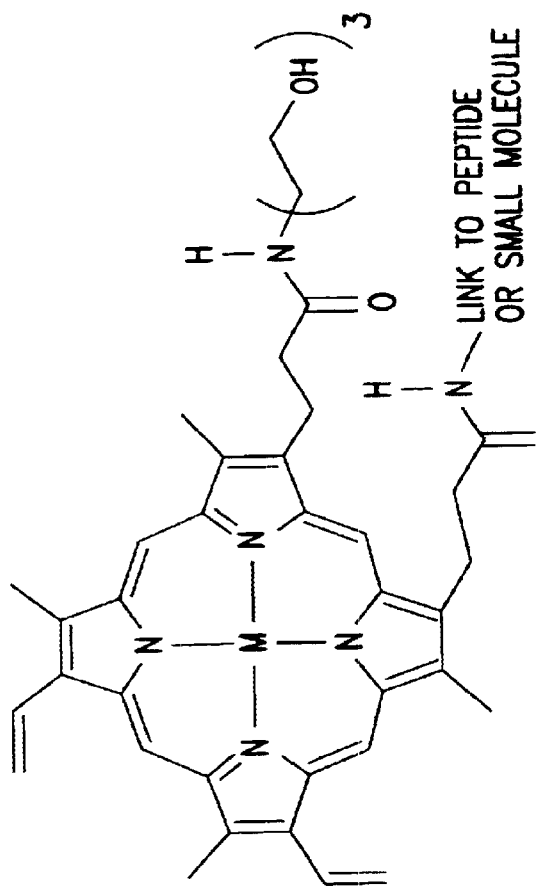
FIG. 7. Schematic of the use of a palladium porphyrin complex with a lead compound to better define the protein target. The typical situation demonstrates a low affinity binding of the lead compound to the protein target, making identification of the protein target difficult. Linking the lead compound to a palladium porphyrin molecule (as demonstrated in the chemical structure) allows photochemically-initiated cross-linking to the target protein.

A model has been proposed for how the ruthenium bipyridyls react with a target protein following light activation (FIG. 1). When $Ru(II)bpy_3^{2+}$ is photolyzed in the presence of persulfate, $Ru(III)bpy_3^{3+}$ and a sulfate radical are generated. Crosslinking can then occur through the formation of 2,2'-dityrosine-coupled adducts or between a tyrosyl radical and other nucleophilic side chains. Paladium porphyrins, as depicted in FIG. 7., also form adducts following photoactivation in the presence of an electron donor such as persulfate.

Ruthenium bipyridyls have been used in a number of detection and chromatographic techniques making use of their electrochemiluminescence properties. Examples include detection of aromatic amines (Bolden et al., 1988), erythromycin (Ridlen et al., 1997), oxygen (Velasco-Garcia et al., 1997) and small peptides like Dynorphin A (Woltman et al., 1999). Ruthenium bipyridols have also been incorporated into a novel equilibrium immunoassay making use of its electrochemiluminescent properties for potential detection of a number of antigens (Grimshaw et al., 1997). Patents making use of ruthenium pyridyls concern photographic techniques (U.S. Pat. No. 5,006,446 and U.S. Pat. No. 4,818,665, both incorporated herein by reference) and photolysis of water (U.S. Pat. No. 4,105,517, incorporated herein by reference).

Palladium porphyrins have been used extensively in oxygen detection in a number of biologic scenarios. These include oxgen measurement in skeletal muscle (Hogan, 1999), retina (Blumenroder et al., 1997), and vasculature (Torres-Filho et al., 1996). Several patents exist on these types of oxygen sensors utilyzing palladium porphyrins, including U.S. Pat. No. 5,564,419, U.S. Pat. No. 5,043,286 and U.S. Pat. No. 4,810,655, incorporated herein by reference. Palladium porphyrins have also been used to modify antibodies for use in diagnostic and therapeutic applications (Mel'nikova et al., 1997; Martsev et al., 1995). The antibody modification made use of a hydroxysuccinimide ester of a palad ium porphyrin rather than direct use of the compound.

The crosslinking reaction involving ruthenium bipyridyls and palladium porphyrins utilizes an electron acceptor for the reaction. "Electron acceptor" is defined to mean any easily reduced molecule that will facilitate the cross linking reactions. In preferred embodiments, ammonium persulfate is used as the electron acceptor.

The crosslinking reaction involving ruthenium bipyridyls and palladium porphyrins is photo activated using visible light. In theory, a broad spectrum of light sources can be used to activate the reaction. Examples given in this application range from a handheld flashlight to a high intensity light bulb to a Xenon lamp. General requirements for the light source is that it has a wavelength of greater than 380 nm but less than 800 nm., the intensity of the light is between 1 watt and 1000 watts, for a period of time between 30 milliseconds and 30 seconds.

2. Methods of Using Ruthenium Bipyridyl and Palladium Porphyrin Crosslinkers

Three broad uses of ruthenium bipryidyl and palladium porphyrin crosslinkers are contemplated in the present invention. The first involves the use of the crosslinkers to identify novel molecular interactions in complex biologic mixtures. This can be done when none of the molecules involved in a biologic system are known, and serve to identify and purify components of a system. Alternatively, the crosslinkers can be used to first form covalent-adducts or chimeras with one known comnponent of a biologic system, and then this modified component is added back into a biologic system such that novel proteins that interact with the known component can be identified and purified. The molecules maybe proteins, lipids, carbohydrates, or nucleic acids.

The second use of ruthenium bipryidyl and palladium porphyrin crosslinkers is to modify a known first component which may be a compound, peptide or protein such that following photoactivation it forms a covalent bond with a second component which may be a compound, peptide or protein. In this way, the two components are linked permanently together. This can have utility for labeling components of a system, for drug delivery to specific targets, trapping a two component system either in an activated or non-activated state, and linking haptens to carriers for immunization.

The following sections detail these general uses and details of how to implement them.

A. Use of Crosslinkers When Molecules are Uncharacterized.

The first method involves the use of the crosslinkers to identify novel protein-protein and protein-non-protein interactions in complex biologic mixtures. This can be done when the proteins involved in a biologic system are not well characterized as a way of identifying or purifing components of a system, or when the proteins are known but their interactions or binding proteins are not.

For example, the structures, organization and functions of cytoskeletal filaments, membranes, extracellular matrices and other biological systems depend on specific interactions between many macromolecules. A major problem which faces biologists is to identify these specific interactions. One approach is to isolate macromolecules and examine their interactions in vitro, but this approach is limited by the difficulty of extrapolating results to the situation in living cells. The in vitro approach needs to be supplemented with methods for analyzing protein-protein interactions in situ.

The ability to use a photoactivatable crosslinker that is membrane permeable will be very beneficial. Crosslinkers of the present invention can be added to in vitro or in vivo systems containing proteins, peptides or compounds. Photoactivation of the mixture will result in crosslinking of components of the systems. The fact that the ruthenium bipryidyl and palladium porphyrin crosslinkers described herein are activated by visible light is an advantage in that there is very little pertubation of the biologic system being studied. This is not the case when photocrosslinkers requiring UV light for activation are used.

B. Crosslinking of Known Compounds to Unknowns

The crosslinkers can also be used to first form covalent adducts or chimeras with one known component of a biologic system, and then this modified component is added back into a biologic system such that novel proteins that interact with the known component can be identified and purified. Potential compounds, peptides or proteins can be anything that is amenable to being modified by the crosslinkers described herein.

The compound, peptide or protein would be conjugated in vitro to generate a reagent that could then be added to either an in vitro or in vivo system. Following incubation to let the conjugated reagents interact with target sites, one would photoactivate the crosslinkers to covalently bond the conjugated reagent to its target site. This will serve as a means for identifying receptors, subunits of multicomponent systems, enzymes, binding sites, and so on that the known compound, peptide or protein initially conjugated to the crosslinker is interacting with in the system. Knowing the identity of the conjugated compound, peptide or protein will allow purification and subsequent analysis of the crosslinked molecule. The converse experiment, where the target initially carries the linker, also may be performed.

In certain embodiments, the present invention can be combined with traditional methodologies of peptidomimetics and rational drug design. Peptidomimetics can be described as compounds derived from peptides and proteins and are obtained by structural modification using unnatural amino acids, conformational restraints, isosteric replacement, cyclisation, etc. The peptidomimetics bridge the gap between simple peptides and the nonpeptide synthetic structures and as such may be useful in delineating pharmacores and in helping to translate peptides into small nonpeptide compounds. Peptidomimetic is sometimes used in a broad sense to designate organic molecules mimicking some properties of peptide ligands.

Certain mirnetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for a target protein. This could be accomplished by x-ray crystallography, computer modeling or by a combination of both approaches. An alternative approach, "alanine scan," involves the random replacement of residues throughout molecule with alanine, and the resulting effect on fumction determined. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore.

Many screens and design methodologies for identifying novel candidate compounds, peptides and proteins are known, including phage display, yeast two hybrid systems, and combinatorial chemistry approaches. This methodology can be exploited for identifying candidate compounds, peptides and proteins which interact with a target of interest. The candidate can be conjugated with crosslinkers as described in the present application, added to a test system, and then photocrosslinked to target molecules. Crosslinkined species could then be isolated and characterized to further identify and further define improved candidate compounds, i.e. ones with preferred binding characteristics and specificities.

In certain embodiments of the present invention, candidate peptides or polypeptides are derived from screening technologies like phage display libraries. The display of peptides and proteins on the surface of bacteriophage represents a powerful new methodology for carrying out molecular evolution in the laboratory. The ability to construct libraries of enormous molecular diversity and to select for molecules with predetermined properties, has made this technology applicable to a wide range of problems. The origins of phage display date to the mid-1980's when George Smith first expressed a foreign segment of a protein on the surface of bacteriophage M13 virus particles. As a test case he fused a portion of the gene encoding the EcoR I endonuclease to the minor capsid protein pIII (Smith, 1985). Using an polyclonal antibody specific for the endonuclease, Smith demonstrated that phage containing the EcoR I-gill fusion could be enriched more than 1000-fold from a mixture containing wild-type (non-binding) phage with an immobilized polyclonal antibody. From these first experiments emerged two important concepts. First, using recombinant DNA technology, it should be possible to build large libraries (i.e., $10^8$) wherein each phage displays a unique random peptide. Second, the methodology provides a direct physical link between phenotype and genotype. That is, every displayed molecule has an addressable tag via the DNA encoding that molecule. Because of the ease and rapidity of DNA sequence analysis, selected molecules can be quickly identified. It is interesting to note that the idea of addressable tags is also now being adopted in some combinatorial chemical libraries (Needels et al., 1993; Ohlmeyer et al., 1993). Within a few years of George Smith's experiments the first phage displayed random peptide libraries were assembled (Cwirla et al, 1990; Devlin et al., 1990; Scott and Smith, 1990), followed shortly by reports that properly folded and functional proteins could also be displayed on the surface of M13 (Bass et al., 1990; McCafferty et al., 1990).

C. Crosslinking of Known Compounds

The use of ruthenium bipryidyl and palladium porphyrin crosslinkers attached to known or candidate compounds, peptides or proteins is specifically contemplated in the present invention. The ability to photocrosslink at will either in vitro or in vivo to covalently attach a compound, peptide or protein to a target site can increase its efficacy or utility, as shown in the following examples. Examples include compounds such as drugs or prodrugs (antibiotics, chemotherapeutics, protease inhibitors, enzyme inhibitors, analgesics and so on), nucleic acids (ribozymes, antisense oligos and so on), peptides such as peptide hormones or peptidomimetics, and proteins such as tumor suppressors, inducers of apoptosis, enzymes, cytokines, toxins, antibodies, transcription factors and regulators, cell cycle regulators, chemokines, and so on. Specific examples of these types of compounds, peptides or proteins are given below.

i) Labels

It is contemplated by the current application that ruthenium bipryidyl and palladium porphyrin crosslinkers can be used to attach labels to proteins, peptides or compounds. Several different types of labels can be used, as detailed herein. To provide a detecting means, the protein will have an associated label to allow detection. Preferably, this will be an enzyme that will generate color development upon incubating with an appropriate chromogenic substrate. Thus, for example, a urease, glucose oxidase, alkaline phosphatase or hydrogen peroxidase-conjugated protein will being incubated with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. No. Nos.

5,310,687, 5,238,808 and 5,221,605. Other moieties which may be conjugated to proteins include radionuclides such as $^{3}H$, $^{125}I$, $^{131}I$ $^{32}P$, $^{35}S$, $^{14}C$, $^{51}Cr$, $^{36}Cl$, $^{57}CO$, $^{58}Co$, $^{59}Fe$, $^{75}Se$, $^{152}Eu$, and $^{99m}Tc$.

ii) Drugs

The use of ruthenium bipryidyl and palladium porphyrin crosslinkers attached to known or candidate drugs is also contemplated in the present invention. As examples of known drugs that could be modified with crosslinking agents to increase their effectiveness, two general classes of drugs are described below, namely antibiotics such as fluoroquinolines, and chemotherapeutics. The final section describes techniques for using ruthenium bipryidyl and palladium porphyrin crosslinkers attached to candidate drugs obtained from screens or rational drug design schemes.

A. Antibiotics

The therapeutic class of compounds known as the fluoroquinolones is widely known and used in antibacterial treatments (U.S. Pat. No. 4,448,962; DE U.S. Pat. No. 3,142,854, EP 206283; U.S. Pat. No. 4,499,091; U.S. Pat. No. 4,704,459; U.S. Pat. No. 4,795,751; U.S. Pat. No. 4,668,784; U.S. Pat. No. 5,532,239 each specifically incorporated herein by reference).

Particularly preferred fluoroquinolones that can be modified with crosslinkers of the present invention include but are not limited to pefloxacin, norfloxacin, ciprofloxacin, ofloxacin, sparfloxacin, grepafloxacin, Bay 12-8039, trovafloxacin, DU6859a, sarafloxacin, LB20304, levofloxacin, enoxacin, fleroxacin, lomefloxacin, temofloxacin, amifloxacin, tosufloxacin, flumequine, rufloxacin, clinafloxacin and the like.

Other antibiotics that can be conjugated with ruthenium bipryidyl and palladium porphyrin crosslinkers include aminoglycosides such as hygromycin B, Kanamycin and streptomycin, antifungal antibiotics such as amphotericin B, cyclohexamide, and nystatin, antineoplastic antibiotics, including mitomycin C, puromycin, and streptozocin, antitubercular antibiotics, including rifamrpin and capreomycin, lactam antibiotics such as amoxicillin and penicillin, macrolide antibiotics, including nystatin and brefelden A, peptide antibiotics, including echinomycin and gramicicdin, tetracyclines, chloramphenicol and tunicamycin.

B. Chemotherapeutics

A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, nmtomycin C, cisplatin (CDDP), verapamil, and podophyllotoxin.

Agents that directly cross-link nucleic acids, specifically DNA, are envisaged to facilitate DNA damage leading to cell death. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

iii) Peptides

The use of ruthenium bipryidyl and palladium porphyrin crosslinkers attached to known or candidate peptides is also contemplated in the present invention. As examples of known peptides that could be modified with photocrosslinking agents to increase their effectiveness include peptide hormones. Alternatively, techniques for using ruthenium bipryidyl and palladium porphyrin crosslinkers attached to candidate peptides obtained from screens such as phage display are described.

Peptide hormones claimed herein for crosslinking are grouped into three classes with specific examples given for each. These classes are defined by the complexity of their post-translational processing. Class I is represented by Growth Hormone, Prolactin and Parathyroid hormone. A more extensive list of human peptides that are included in Class I is given in Table 2. These require relatively limited proteolytic processing followed by storage and stimulated release from secretory granules. Class II is represented by Insulin and Glucagon. A more extensive list of human peptide hormones that are included in Class II are given in Table 3. Further proteolytic processing is required, with both endoproteases and carboxypeptidases processing of larger precursor molecules occurring in the secretory granules. Class III is represented by Amylin, Glucagon-like Peptide I and Calcitonin. Again, a more extensive list of Class III human peptide hormones is given in Table 4. In addition to the proteolytic processing found in the Class II peptides, amidation of the C-terminus is required for proper biological function. Examples of engineering, expression of all three of these classes of peptide hormones in a neuroendocrine cell are found in this patent.

TABLE 1

| Class I Human Peptide Hormones |
| --- |
| Growth Hormone |
| Prolactin |
| Placental Lactogen |
| Luteinizing Hormone |
| Follicle-stimulating Hormone |
| Chorionic Gonadotropin |
| Thyroid-stimulating Hormone |
| Leptin |

TABLE 2

| Human Peptide Hormones Processed by Endoproteases from Larger Precursors |
| --- |
| Adrenocorticotropin (ACTH) |
| Angiotensin I and II |

TABLE 2-continued

Human Peptide Hormones Processed by
Endoproteases from Larger Precursors

β-endorphin
β-Melanocyte Stimulating Hormone (β-MSH)
Cholecystokinin
Endothelin I
Galanin
Gastric Inhibitory Peptide (GIP)
Glucagon
Insulin
Lipotropins
Neurophysins
Somatostatin

TABLE 3

Amidated Human Peptide Hormones

Calcium Metabolism Peptides:

Calcitonin
Calcitonin Gene related Peptide (CGRP)
β-Calcitonin Gene Related Peptide
Hypercalcemia of Malignancy Factor (1-40)(PTH-rP)
Parathyroid Hormone-related protein (107-139)(PTH-rP)
Parathyroid Hormone-related protein (107-111)(PTH-rP)
Gastrointestinal Peptides:

Cholecystokinin (27-33)(CCK)
Galanin Message Associated Peptide, Preprogalanin (65-105)
Gastrin I
Gastrin Releasing Peptide
Glucagon-like Peptide (GLP-1)
Pancreastatin
Pancreatic Peptide
Peptide YY
PHM
Secretin
Vasoactive Intestinal Peptide (VIP)
Pituitary Peptides:

Oxytocin
Vasopressin (AVP)
Vasotocin
Enkephalins:

Enkephalinamide
Metorphinamide (Adrenorphin)
Alpha Melanocyte Stimulating Hormone (alpha-MSH)
Atrial Natriuretic Factor (5-28)(ANF)
Amylin
Amyloid P Component (SAP-1)
Corticotropin Releasing Hormone (CRH)
Growth Hormone Releasing Factor (GHRH)
Luteinizing Hormone-Releasing Hormone (LHRH)
Neuropeptide Y
Substance K (Neurokinin A)
Substance P
Thyrotropin Releasing Hormone (TRH)

iv) nucleic acids

The use of ruthenium bipryidyl and palladium porphyrin crosslinkers is also anticipated in this application with nucleic acids. Nucleic acids alredy have the ability to hybridize to specific sequences through complementary base pairing. The ability to add a photocrosslinking step in the process to covalently attach nucleic acids would be beneficial. Examples of two potential methodologies, namely antisense oligos and ribozymes, described below.

A. Antisense Oligos

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host-animal, including a human subject.

Antisense oligos may be designed to bind to the promoter and other control regions, exons, introns or even exon-intron boundaries of a gene. It is contemplated that the most effective antisense oligos will include regions complementary to intron/exon splice junctions. Thus, it is proposed that a preferred embodiment includes an antisense oligos with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular fumction is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Particular oncogenes that are targets for antisense constructs are ras, myc, neu, raf, erb, src, fms, jun, trk, ret, hst, gsp, bcl-2 and abl. Also contemplated to be useful will be anti-apoptotic genes and angiogenesis promoters.

B. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this emnbodiment will include angiogenic genes such as VEGFs and angiopoeiteins as well as the oncogenes (e.g., ras, myc, neu, raf, erb, src, fms, jun, trk, ret, hst, gsp, bcl-2, EGFR, grb2 and ab1).

v) Proteins

It is contemplated that several different classes of proteins can be modified with ruthenium bipryidyl and palladium porphyrin crosslinkers such that once added to a biologic system they can be subsequently photoactivated and covalently attached to their target. Exemplary proteins are listed below.

A. Tumor Suppressors p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as SV40 large-T antigen and adenoviral E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proli-ferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53, in as much as mutations in p53 are known to abrogate the tumor suppressor capability of wild-type p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysftmctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect also has been demonstrated on transfection of wild-type, but not mutant, p53 into human lung cancer cell lines (Takahasi et-al., 1992). p53 appears dominant over the mutant gene and will select against proliferation when transfected into cells with the mutant gene. Normal expression of the transfected p53 dbes not affect the growth of normal or non-malignant cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit $p16^{INK4}$. The $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyper-phosphorylation of the Rb protein. p16 also is known to regulate the fiunction of CDK6.

$p16^{INK4}$ belongs to a newly described class of CDK-inhibitory proteins that also includes $p15^{INK4B}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type $p16^{INK4}$ function by transfection with a plasmid expression vector reduced colony formation by some human cancer cell lines (Okamoto, 1994; Arap, 1995). Delivery of p16 with adenovirus vectors inhibits proliferation of some human cancer lines and reduces the growth of human tumor xenografts.

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly, homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include p21, p15, BRCA1, BRCA2, IRF-1, PTEN, RB, APC, DCC, NF-1, NF-2, WT-1, MEN-I, MEN-II, zacl, p73, VHL, FCC, MCC, DBCCR1, DCP4 and p57.

B. Inducers of Apoptosis

Inducers of apoptosis, such as Bax, Bak, Bcl-$X_s$, Bad, Bim, Bik, Bid, Harakiri, Ad E1B, Bad, ICE-CED3 proteases, TRAIL, SARP-2 and apoptin, similarly could find use according to the present invention.

C. Enzymes

Various enzyme genes are of interest according to the present invention. Such enzymes include cytosine deaminase, adenosine deaminase, hypoxanthine-guanine phosphoribosyltransferase, galactose-1-phosphate uridyltransferase, phenylalanine hydroxylase, glucocerbrosidase, sphingomyelinase, $\alpha$-L-iduronidase, glucose-6-phosphate dehydrogenase, HSV thymidine kinase and human thymidine kinase and extracellular proteins such as collagenase, matrix metalloprotease, RSKB, RSK1, RSK2, RSK3, thrombospondin, fibronectin and plasminogen. In other embodiments of the present invention, the use of anti-angiogenic factors are contemplated.

D. Cytokines

Another class of genes that is contemplated for use in the present invention include interleukins and cytokines. Interleukin 1, IL-2, IL-3, IL-4, IL-5, IL-6, IL-7, IL-8, IL-9, IL-10, IL-11, IL-12, IL-13, IL-14, IL-15, $\beta$-interferon, $\alpha$-interferon, $\gamma$-interferon, angiostatin, thrombospondin, endostatin, METH-1, METH-2, GM-CSF, G-CSF, M-CSF and tumor necrosis factor.

E. Toxins

Various toxins are also contemplated to be useful as part of the present invention. These toxins include bacterial toxins such as ricin A-chain (Burbage, 1997), diphtheria toxin A (Massuda et al., 1997), pertussis toxin A subunit, *E. coli* enterotoxin toxin A subunit, cholera toxin A subunit and pseudomonas toxin c-terminal.

F. Single Chain Antibodies

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, growth factors, hormones, enzymes, transcription factors or receptors. Also contemplated are secreted antibodies, targeted to serum, against angiogenic factors (VEGF/VSP; $\beta$FGF; $\alpha$FGF) and endothelial antigens necessary for angiogenesis (i.e., V3 integrin). Specifically contemplated are growth factors such as transforming growth factor and platelet derived growth factor.

G. Transcription Factors and Regulators

Another class of genes that can be applied in an advantageous combination are transcription factors. Examples include C/EBP$\alpha$, I$\kappa$B, Nf$\kappa$B, Par-4 and C/EBP$\alpha$.

H. Cell Cycle Regulators

Cell cycle regulators provide possible advantages, when combined with other genes. Such cell cycle regulators include p27, p16, p21, p57, p18, p73, p19, p15, E2F-1, E2F-2, E2F-3, p107, p130 and E2F-4. Other cell cycle regulators include anti-angiogenic proteins, such as soluble Fltl (dominant negative soluble VEGF receptor), soluble Wnt receptors, soluble Tie2/Tek receptor, soluble hemopexin domain of matrix metalloprotease 2 and soluble receptors of other angiogenic cytokines (e.g. VEGFR1/KDR, VEGFR3/Flt4, both VEGF receptors).

I. Chemokines

Genes that code for chemokines also may be used in the present invention. Chemokines generally act as chemoattractants to recruit immune effector cells to the site of chemokine expression. It may be advantageous to express a particular chemokine gene in combination with, for example, a cytokine gene, to enhance the recruitment of other imnmune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

J. Secreted Proteins

Expression of several proteins that are normally secreted can be engineered into neuroendocrine cells. The cDNA's encoding a number of useful human proteins are available. Examples would include soluble CD-4, Factor VIII, Factor IX, von Willebrand Factor, TPA, urokinase, hirudin, interferons, TNF, interleukins, hematopoietic growth factors, antibodies, albumin, leptin, transferin and nerve growth factors.

3. Purification of Crosslinked Molecules

The present invention also provides techniques for purifying compounds, polypeptides, or peptides following crosslinking with ruthenium bipyridyl or palladium porphyrin. The term "purified compounds, polypeptides, or peptides" as used herein, is intended to refer to a composition, isolatable from biologic sources, wherein the crosslinked compound, polypeptide, or peptide is purified to any degree relative to its naturally-obtainable state, i.e., relative to its purity within a cellular extract.

Generally, "purified" will refer to a compound, polypeptide, or peptide composition that has been subjected to fractionation to remove various non-crosslinked compounds, polypeptides, or peptides. Where the term "substantially purified" is used, this will refer to a composition in which the crosslinked compound, polypeptide, or peptide forms the major component of the composition, such as constituting about 50% of the proteins in the composition or more. In preferred embodiments, a substantially purified compound, polypeptide, or peptide will constitute more than 60%, 70%, 80%, 90%, 95%, 99% or even more of the compounds, polypeptides, or peptides in the composition.

A compound, polypeptide or protein that is "purified to homogeneity," as applied to the present invention, means that the compound, polypeptide or protein has a level of purity where the compound, polypeptide or protein is substantially free from other proteins and biological components. For example, a purified compound, polypeptide or protein will often be sufficiently free of other components so that it can be identified by various diagnostic methodologies.

Various methods for quantifying the degree of purification of crosslinked compounds, polypeptides, or peptides will be known to those of skill in the art in light of the present disclosure. These include, for example, determining the specific amount of a crosslinked protein in a fraction, or assessing the number of polypeptides within a fraction by gel electrophoresis. Assessing the number of polypeptides within a fraction by. SDS/PAGE analysis will often be preferred in the context of the present invention as this is straightforward and techniques are known to one of ordinary skill in the art.

To purify a crosslinked compound, polypeptide, or peptide a natural or recombinant composition comprising at least some crosslinked proteins, polypeptides, or peptides will be subjected to fractionation to remove various non-crosslinked components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques. Another example is the purification of a crosslinked protein using a specific binding partner. Such purification methods are routine in the art.

Although preferred for use in certain embodiments, there is no general requirement that the crosslinked protein, polypeptide, or peptide always be provided in their most purified state. Indeed, it is contemplated that less substantially purified protein, polypeptide or peptide, which are nonetheless enriched in crosslinked protein compositions, relative to the natural state, will have utility in certain embodiments. These include, for example, antibody generation where subsequent screening assays using purified crosslinked proteins are conducted.

Any of a wide variety of chromatographic procedures may be employed to purify crosslinked compounds, peptides or proteins. For example, thin layer chromatography, gas chromatography, high performance liquid chromatography, paper chromatography, affinity chromatography or supercritical flow chromatography may be employed.

Partition chromatography is based on the theory that if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillary action draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention are well known to those skilled in the art.

4. Detection Methods

In still further embodiments, the present invention concerns methods for binding, purifying, removing, quantifying or otherwise generally detecting biological components. The peptide- or small molecule-metal ligand conjugates prepared in accordance with the present invention may be employed to detect target polypeptides or peptides. The steps of various useful immunodetection methods have been described in the scientific literature, such as, e.g., Nakamura et al. (1987), incorporated herein by reference.

It is contemplated that these various immunodetection methods can be modified to make use of the peptide- or small molecule-metal ligand conjugates as a substitute for the primary antibodies that are generally used. Immunoassays based on immunodetection, in their most simple and direct sense, are binding assays. Certain preferred immunoassays that can be modified to use the peptide- or small molecule-metal ligand conjugates are the various types of enzyme linked immunosorbent assays (ELISAs) and radioimmunoassays (RIA) as well as immunohistochemical detection using tissue sections known in the art. In addition, other detection techniques, such as western blotting, dot blotting, FACS analyses, and the like can also be modified to use peptide- or small molecule-metal ligand conjugates.

These methods include methods for purifying proteins, polypeptides or peptides. In these instances, the peptide- or small molecule-metal ligand conjugates removes the target polypeptide or peptide component from a sample. The peptide- or small molecule-metal ligand conjugates will preferably be linked to a solid support, such as in the form of a column matrix, and the sample suspected of containing the target polypeptide component will be applied to the immobilized peptide- or small molecule-metal ligand conjugates. The unwanted components will be washed from the column, leaving the target complexed to the immobilized column, which target is then collected by removal from the column.

The binding methods also include methods for detecting or quantifying the amount of a target polypeptide reactive component in a sample, which methods require the detection or quantification of any complexes formed during the binding process. Here, one would obtain a sample suspected of containing a target polypeptide or peptide, and contact the sample with an peptide- or small molecule-metal ligand conjugates capable of binding the target, and then detect or quantify the amount of complexes formned under the specific conditions.

Contacting the chosen biological sample with the peptide- or small molecule-metal ligand conjugates under conditions effective and for a period of time sufficient to allow the formation of complexes is generally a matter of simply adding the peptide- or small molecule-metal ligand conjugates to the sample and incubating the mixture for a period of time long enough for the peptide- or small molecule-metal ligand conjugates to form complexes with, i.e., to bind to, any target protein, peptide or polypeptide present. After this time, the sample, such as a tissue section, ELISA plate, dot blot or wester blot, will generally be washed to remove any non-specifically bound species, allowing only those peptide- or small molecule-metal ligand conjugates-specifically bound within the complexes to be detected.

In general, the detection of complex formation is well known in the art and may be achieved through the application of numerous approaches analogous to immunodetection methods. These methods are generally based upon the detection of a label or marker, such as any of those radioactive, fluorescent, biological or enzymatic tags. U.S. Pat. Nos. concerning the use of such labels include 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The peptide- or small molecule-metal ligand conjugate employed in the detection may itself be linked to a detectable label, wherein one would then simply detect this label, thereby allowing the amount of the primary complexes in the composition to be determined. Alternatively, the first peptide- or small molecule-metal ligand conjugates that becomes bound within the primary complexes may be detected by means of a second binding ligand that has binding affinity for the peptide- or small molecule-metal ligand conjugates. In these cases, the second binding ligand may be linked to a detectable label. The second binding ligand may be an antibody. The primary complexes are contacted with the labeled, secondary binding ligand, or antibody, under conditions effective and for a period of time sufficient to allow the formation of secondary complexes. The secondary complexes are then generally washed to remove any non-specifically bound labeled secondary antibodies or ligands, and the remaining label in the secondary complexes is then detected.

Further methods include the detection of primary complexes by a two step approach. A second binding ligand, such as an antibody, that has binding affinity for the peptide- or small molecule-metal ligand conjugates is used to form secondary complexes, as described above. After washing, the secondary complexes are contacted with a third binding ligand or antibody that has binding affinity for the antibody, again under conditions effective and for a period of time sufficient to allow the formation of immune complexes. The third ligand or antibody is linked to a detectable label, allowing detection of the tertiary immune complexes thus formed. This system may provide for signal armplification if this is desired.

5. Detection Kits

In still further embodiments, the present invention concerns detection kits for use with the detection methods described above. As the peptide- or small molecule-metal ligand conjugates are generally used to detect target polypeptides or peptides, the peptide- or small molecule-metal ligand conjugates will preferably be included in the kit. However, kits including both such components may be provided. The detection kits will thus comprise, in suitable container means, a first peptide- or small molecule-metal ligand conjugate that binds to a target polypeptide or peptide, and optionally, an immunodetection reagent and further optionally, a target polypeptide or peptide.

In certain embodiments, the peptide- or small molecule-metal ligand conjugates that binds to the target protein, polypeptide or peptide may be pre-bound to a solid support, such as a column matrix or well of a microtitre plate.

The detection reagents of the kit may take any one of a variety of forms, including those detectable labels that are associated with or linked to the given peptide- or small molecule-metal ligand conjugates. Detectable labels that are associated with or attached to a secondary binding ligand are also contemplated. Exemplary secondary ligands are those secondary antibodies that have binding affinity for the first peptide- or small molecule-metal ligand conjugates.

Further suitable detection reagents for use in the present kits include the two-component reagent that comprises a secondary antibody that has binding affinity for the peptide- or small molecule-metal ligand conjugates, along with a second antibody that has binding affinity for the first antibody, the second antibody being linked to a detectable label. As noted above, a number of exemplary labels are known in the art and all such labels may be employed in connection with the present invention.

The kits may further comprise a suitably aliquoted composition of the target peptide or polypeptide, whether labeled or unlabeled, as may be used to prepare a standard curve for a detection assay. The kits may contain peptide- or small molecule-metal ligand conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the peptide- or small molecule-metal ligand conjugates may be placed, and preferably, suitably aliquoted. Where target polypeptide or peptide, or a second or third binding ligarnd or additional component is provided, the kit also will generally contain a second, third or other additional container into which this ligand or component may be placed. The kits of the present invention also will typically include a means for containing the peptide- or small molecule-metal ligand conjugates, target, and any other reagent containers in close confinement for commercial sale. Such containers may include injection or blow-molded plastic containers into which the desired vials are retained.

6. Formulations of Crosslinkers and Crosslinked Compounds

Pharmaceutical compositions of the present invention will generally comprise an effective amount of the ruthenium bipryidyl and palladium porphyrin crosslinked compound, peptide or protein dissolved or dispersed in a pharmaceutically acceptable carrier or aqueous medium. The pharmaceutical composition may further comprise a ruthenium bipryidyl and palladium porphyrin crosslinker composition.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The ruthenium bipryidyl and palladium porphyrin crosslinked compound, peptides or proteins of the present invention will often be formulated for parenteral administration, e.g., formulated for injection via the intravenous, intramuscular, sub-cutaneous or other such routes, including direct instillation into an infected or diseased site. The preparation of an aqueous composition that contains a crosslinked agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection also can be prepared; and the preparations also can be emulsified.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The ruthenium bipryidyl and palladium porphyrin crosslinked compound, peptide or protein compositions can be formulated into a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifingal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-dryng and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like also can be employed.

Suitable pharmaceutical compositions in accordance with the invention will generally include an amount of the ruthenium bipryidyl and palladium porphyrin crosslinked compound, peptide or protein admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that, for human administration, preparations should meet sterility, pyrogenicity, general safety and purity standards as required by the FDA Office of Biological Standards.

The therapeutically effective doses are readily determinable using an animal model. Experimental animals are frequently used to optimize appropriate therapeutic doses prior to translating to a clinical environment. Such models are known to be very reliable in predicting effective treatment strategies in humans.

In addition to the compounds formulated for parenteral administration, such as intravenous or intramuscular injection, other pharmaceutically acceptable forms also are contemplated, e.g., tablets or other solids for oral administration, time release capsules, lipdsomal forms and the like. Other pharmaceutical formulations may also be used, dependent on the condition to be treated.

For oral administration the ruthenium bipryidyl and palladium porphyrin crosslinked compounds, peptides or proteins of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

7. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Design of A Visible Light-Initiated Protein Cross-Linking Reaction

Chemical cross-linking is a potentially useful technique for probing architecture of multi-protein complexes. However, analyses using typical bifunctional cross-linkers often suffer from poor yields and large-scale modification of nucleophilic side chains can result in artifactual results due to structural destabilization. The inventors report here the de novo design and development of a new kind of protein cross-linking reaction that employs a photo-generated oxidant to mediate rapid and efficient cross-linking of associated proteins. The process involves brief photolysis of tris-bipyridylruthenium(II) dication with visible light in the presence of the electron acceptor ammonium persulfate and the proteins of interest. Very high yields of cross-linked products can be obtained with irradiation times of less than one second. This chemistry obviates many of the problems associated with standard cross-linking reagents.

This example details the design of a photo-activated reagent that cross-links closely associated proteins very rapidly and in high yield. Rapid cross-linking with a photo-activated reagent is useful for probing the dynamics of protein-protein interactions in a particular complex as it proceeds through a catalytic cycle. This kind of application is beyond the reach of current cross-linking technology. In particular, a visible light-triggered reaction would be useful for probing protein-protein interactions in living cells or in erode extracts since cells contain few visible chromophores, but many molecules that absorb UV light.

The photolysis of the ruthenium(II) tris-bipyridyl dication (Ru(II)bpy$_3^{2+}$) in the presence of ammonium persulfate was explored as a method to generate inactive intermediates that might bring about efficient cross-linking of associated proteins. The logic behind this choice is as follows. Ru(II)bpy$_3^{2+}$ is an efficient visible light-harvesting molecule, with a $\lambda_{max}$ of 452 nm in water and a molar extinction coefficient of about 14,700 M$^{-1}$. Photolysis of this metal complex is known to produce an excited state able to donate an electron to persulfate, resulting in cleavage of the O-O bond (Nickel et al., 1994). The products are Ru(III), a potent one electron oxidant (Gray and Winkler, 1996; Wherland and Gray, 1976; Yocom et al., 1982), the sulfate radical, which should be a good hydrogen atom abstraction agent, and sulfate anion. As shown in FIG. 1, reasonable mechanisms can be proposed by which these species can bring about protein cross-linking. Ru(III)-mediated formnation of a tyrosyl radical is proposed as an initiating step. Coupling of this radical with one of several possible nucleophiles and subsequent removal of a hydrogen atom by the persulfate could consummate the reaction. This scheme is precedented by previous work on the oxidative cross-linking of proteins mediated by chemically-activated metal complexes from the inventors laboratory and others (Bertrand et al., 1997; Fancy and Kodadek, 1997; Mattson et al., 1993; Ji and Ji, 1989; Gaffney, 1985; Bertrand et al., 1997; Jiang et al., 1993; Jiang and Kodedek, 1993; Friedrichson and Kurzchalia, 1998; Schere and Krieg, 1991; Norcum and Warrington, 1998; Kodadek et al., 1989; Hoopes et aL, 1992; Platt and Reece, 1998; Melcher and Johnston, 1995; Fancy and Kodadek, 1997; Nickel et al., 1994; Gray and Winkler, 1996; Wherland and Gray, 1976; Yocom et al., 1982; Stadtman, 1990, Gill et al., 1997, Heinecke et al., 1993; Malencik and Anderson, 1996; Brown et al., 1995; Fancy et al., 1996; Tew and Ortiz de Montellano, 1988; Wilks and Ortiz de Montellano, 1992) as well as intramolecular reactions that occur naturally in certain proteins (Stubbe and Riggs-Gelasco, 1998). Oxidative coupling is an appealing reaction on which to base a photo initiated reaction since it results in the direct coupling of nearby residues without an intervening linker arm (Brown et al., 1998).

EXAMPLE 2

Ru(Ii)Bpy$_3^{2+}$/Persulfate-Mediated Protein Cross-linking is Rapid and Efficient Materials and Methods Proteins. UvsY protein (Kodadek et al., 1989), the 180 amino acid C-terminal domain of yeast TATA-binding protein (TBP) (Hoopes et al., 1992), Gal80 protein (Platt and Reece, 1998), the GST-Gal4 activation domain fusion protein (Melcher and Johnston, 1995) and radiolabeled polypeptide containing the Gal4 activation domain (Fancy and Kodadek, 1997) were purified as described in the literature. Antibody raised against yeast TBP was developed in the inventors lab.

General cross-linking protocol: Cross-linking reactions were carried out in a total volume of 20 μL in a buffer comprised of 15 mM sodium phosphate (pH 7.5), 150 mM NaCl and 0.125 mM Ru(bpy)$_3$Cl$_2$ (Aldrich). Easily oxidized buffer components such as β-mercaptoethanol and dithio-threitol are avoided. Protein concentrations varied depending on the study between 20 μM to 0.01 μM. The solution was placed in a 1.7 mL eppendorf tube positioned parallel to the beam of light at a distance of 50 cm from a 150 Watt xenon arc lamp (Oriel Inc.). APS was added to 25 mM just before irradiation. Light was filtered first through 10 cm of distilled water and then through a 380–2500 nm cut-on filter (Oriel #49470). Exposure time was controlled by shining the light through timed shutters of a Praktica single lens reflex camera with the lens and back cover removed from the camera body. In most experiments the sample was irradiated for 0.5 sec. Immediately following irradiation samples were quenched with 7 μL 4×gel loading buffer (0.2 M Tris, 8% SDS, 2.88 M β-mercaptoethanol, 40% glycerol, 0.4% xylene cyanol, 0.4% broniophenol blue) and heated to 95° C. for 5 min and then separated by electrophoresis through a 10% tricine SDS polyacrylarnide gel. The reducing conditions employed preclude the observation of products linked by disulfide bonds. Proteins were visualized by staining with Coomassie brilliant blue or by Western blot.

Results

Figure 2:
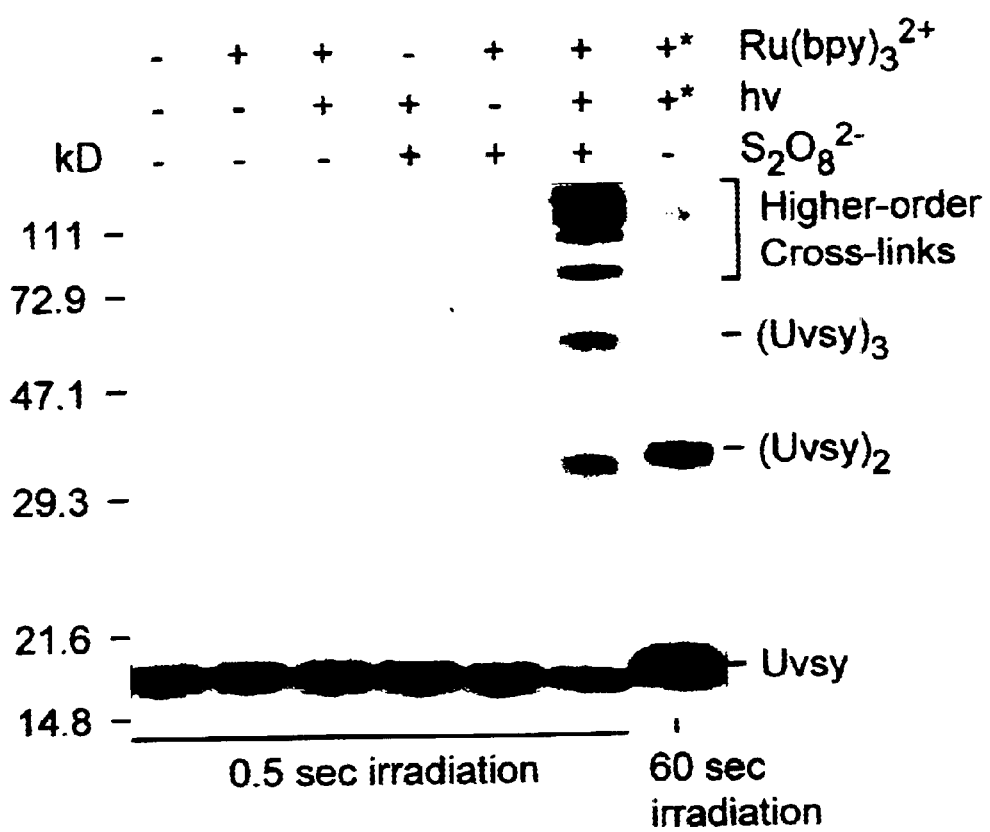
FIG. 2. Treatment of the hexameric UvsY protein with Ru(II)bpy$_3^{2-}$, ammonium persulfate (APS) and light (>380 nm) results in extremely rapid and efficient covalent cross-linking. Shown in a Coomassie-stained denaturing gel. The bands observed in lanes 6 and 7 have mobilities consistent with multimers of the UvsY protein. The metal complex, APS and photolysis are required for the formation of detectable products for short irradiation times (0.5 sec for lanes 1–6). However, readily detectable levels of cross-linking can be obtained in the absence of APS with longer irradiation times (lane 7, 60 sec).

UvsY protein, a native hexamer involved in phage T4 recombination (Beernick and Morrical, 1998; Kodadek et al., 1989), vas photolyzed in the presence of Ru(II)bpy$_3^{2+}$ and ammonium persulfate (APS) using a 105W Xe arc lamp and a filter that cut off light below 380 nm. As seen in FIG. 2, lane 6, photolysis resulted in the production of covalently coupled UvsY multimers. Remarkably, only a 0.5 sec irradiation of visible light was required to achieve the ≈60% yield observed. No reaction was observed in the dark, or when the metal complex was omitted. An approximately-fold lower yield was observed in the absence of APS, demonstrating the requirement of Ru(III) and/or the sulfate radical for efficient cross-linking. Photoexcited Ru(bpy)$_3^{2+}$ is known to be an efficient generator of singlet oxygen (Zhang and Rodgers, 1995; Tanielian et al., 1996), which is expected to be the dominant reaction in the absence of APS. Not surprisingly, this pathway also yields cross-linked products (see lane 7), but of a different nature (as evidenced by their distinct mobilities) and only after much longer irradiation.

The inventors have coined the acronym PICUP (photo-induced cross-linking of unmodified proteins) for this process to distinguish it from very different azide- and benzophenone-based light-initiated reactions sometimes used to probe biomolecular interactions(Chen et al., 1994; Dormnan and Prestwich, 1994). These species, when photolyzed with UV light, generate intermediates that are able to insert into C-H bonds of proteins. They are sometimes used to probe protein-protein interactions by linking then covalently to the protein of interest, often through an engineered cysteine side chain. When the modified protein is docked with the factor(s) with which it interacts, photolysis can lead to protein cross-linking if the azide or benzophenone moiety is near the protein-protein interface. Azide- and benzophenone-based reagents cannot be used "in trans" like the Ru(bpy)$_3^{2+}$-based system described here since they are photoactivated insertion reagents, rather than true crosslinkers. Finally. the η to τ* transitions which must be excited to activate these reagents have very low extinction coefficients compared to Ru(byp)$_3^{2+}$, requiring much longer irradiation times, and $\lambda_{max5}$ in the UV, not the visible, region.

EXAMPLE 3

Photo-Initiated Cross-Linking of Transcription Factors

Figure 3:
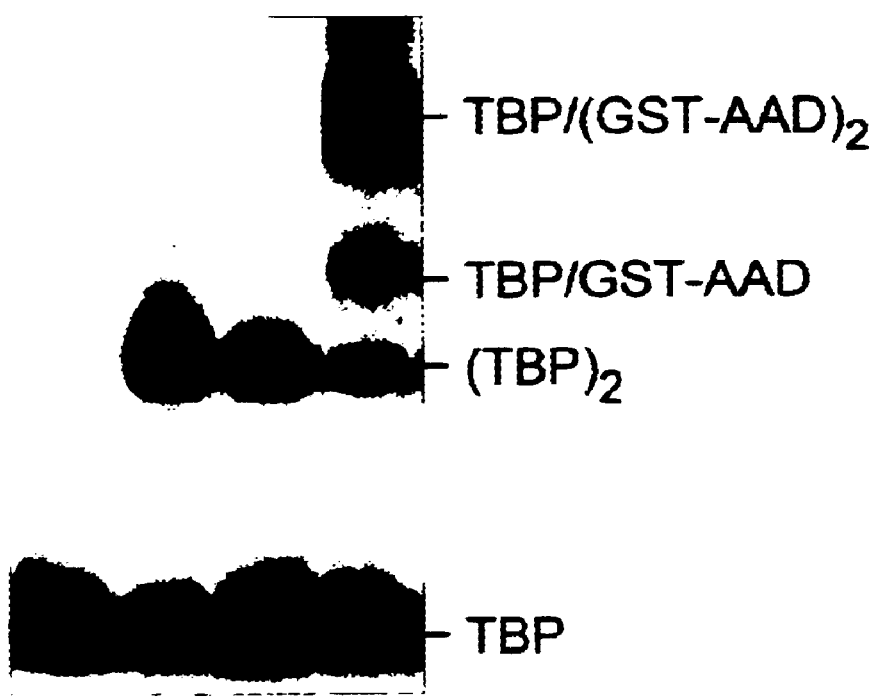
FIG. 3. Photo-initiated cross-linking of the Gal4 activation domain with TATA-binding protein (TBP). The samples exposed to light were irradiated for 0.5 sec with light of >380 nm using a 150W xenon arc lamp. Shown is a Western blot using antibody raised against TBP.

A particular interest of this laboratory (Denison and Kodadek, 1998), and many others, is to elucidate the interactions between transcriptional regulatory factors and the RNA polymerase II transcriptional machinery that is critical for controlling the expression of most eukaryotic genes. To ask if PICUP would be useful for probing interactions between transcription factors, binding of the 34 residue core acidic activation domain (AAD) of the yeast Gal4 protein (Johnston et al., 1987; Van Hoy et al., 1993), a regulator of galactose-metabolizing genes (Johnston, 1987), to the conserved C-terminal 180 residue domain of TATA-binding protein (TBP) was examined. TBP is a basal transcription factor that recognizes the TATA element located in many promoters hand has been proposed to be an important target of many activators (Struhl, 1995), including Gal4 protein (Melcher and Johnston, 1995; Wu et al., 1996). Free TBP is a native homodimer which must dissociate for the protein to bind DNA (Coleman et al., 1995). The complex is comprised of 2:1 molar ratio of AAD to TBP. TBP was mixed with two equivalents of either Glutathione S-tranferase (GST), or a GST-Gal4 AAD fusion protein (Melcher and Johnston, 1995). Ru(II)bpy$_3^{2+}$ and APS were added and the sample was illuminated for 0.5 sec. The results were analyzed by denaturing gel electrophoresis and Western blotting using an antibody specific for TBP. Lane 2 of FIG. 3 shows that in the presence of GST, TBP homodimer was the only TBP-containing product, as expected. The results of this study were essentially identical to that in which GST was omitted (lane 2), demonstrating that PICUP does not couple. GST and TBP, two proteins that do not associate stably. Photolysis of the GST-AAD fusion and TBP resulted in the production of three products. The TBP homodimer was present, but at a reduced level compared to that formed in the absence of the AAD. The majority of product was represented by two bands with the expected apparent molecular masses of GST-34-TBP and (GST-34)$_2$-TBP, respectively, consistent with a 2:1 (GST-AAD-TBP) complex. The overall yield of products was approximately 65%.

Figure 4:
FIG. 4. Cross-linking of a $^{32}$P-labeled Gal4 activation domain (1 μM) to Gal80 protein (0.5 μM). Shown is a phosphorimager scan. In the absence of histidine, cross-linked (Gal4 AAD Gal80)$_2$ and (Gal4 AAD.Gal80)$_4$ are produced in almost quantitative yield. Addition of histidine (7.5 mM) modulates the reaction, producing three products corresponding to the AAD-Gal80p heterodimer, the AAD cross-linked to the Gal80p dimer and the (AAD-Gal80p)$_2$ species.

Another factor known to bind the Gal4 AAD is Gal80protein (Gal80p), a specific repressor of Gal4p (Johnston et al., 1987; Ma and Ptashne, 1987). Like Gal4p, Gal80p is a native homodimer (Van Hoy et al., 1993)) and these dimers associate weakly to form homo-tetramers (K. Melcher, T. K. and S. A. Johnston, submitted). Gal80p and the Gal4 AAD form a tight complex with a 2:2 stoichiometry. As shown in FIG. 4, when a radiolabeled 54 residue polypeptide containing the Gal4 AAD (15) was mixed with a slight excess of purified Gal80p and photolyzed in the presence of Ru(bpy)$_2^{3+}$ and APS for half a sec, almost all of the AAD monomer was converted to cross-linked products. FIG. 4 is a phosphorimage and shows only AAD-containing bands. The lower band in lane 2 has an apparent molecular mass consistent with an AAD$_2$-Gal802 complex. The upper band corresponds to an (AAD-Gal80p)4 species. The formation of this product was not surprising since this study employed μM protein concentrations, and PICUP was able to trap the weak associations between Gal 80p dimers that occur at these levels. As shown in lane 3, the degree of cross-linking can be "toned down" if desired by adding electron-donating amino acids such as histidine to the solution (lane 3). In this case, three product bands were observed, with the apparent molecular masses expected of the aD-Gal 80, AD-Gal 80$_2$ and AD$_2$-Gal 80$_2$ species. Approximately 60% of the monomeric AD remained. This is the spectrum of products expected from the native 2:2 complex. Presumably, the added histidine either competes with the proteins for Ru(III) or sulfate radical, or quenches tyrosyl radicals on the surface of the proteins before diffusional collision with another protein can lead to a cross-link. Histidine does not interfere with the AD-Gal80p association (data not shown). Since PICUP is so efficient, the addition of histidine is a useful method to sort out tight contacts from weak or transient associations since cross-links resulting from the latter are quenched completely, while those resulting from the former are less affected. This "histidine tuning" strategy should also be useful in controlling the extent of multimer formation in experiments using large multi-protein complexes. Exogenous tyrosine also inhibited cross-linking (not shown), consistent with this residue being a target of Ru(III), but this inhibition was so efficient, it blocked all cross-linking and so is not useful as a tuning agent.

EXAMPLE 4

Efficient Cross-Linking Using Various Light Sources

Figure 5:
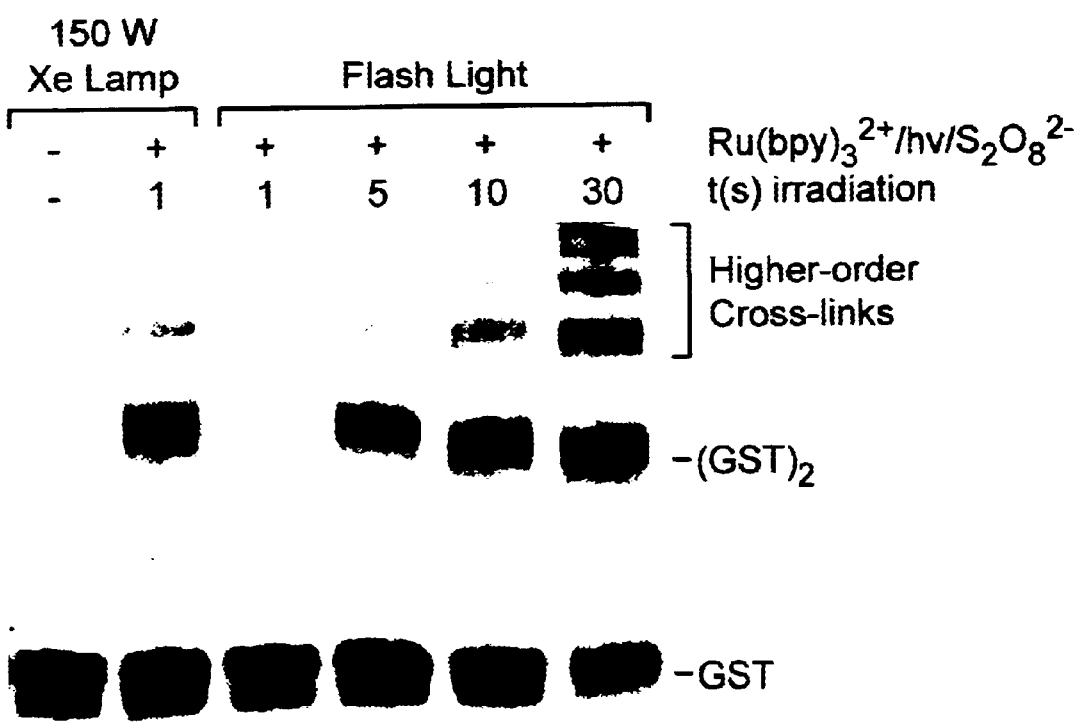
FIG. 5. PICUP does not require an intense light source. Cross-linking of GST under standard conditions was carried out using a 150W xenon lamp or a common flashlight as the light source. Excellent yields can be obtained in the latter case by simply increasing the photolysis time and reducing the lamp-sample distance from 50 cm to 5 cm.

Since PICUP should be of utility to many biochemistry and molecular biology laboratories which do not have access to an intense light source such as the 150W lamp the inventors employed, it was of interest to determine whether more readily available light sources would support the reaction. This was done using GST, which is known to exist as a homodimer (Lim et al., 1994) that further associate into larger aggregates. FIG. 5 shows that even using a standard flashlight, good yields of cross-linking can be achieved under conditions identical to those used with the 150w lamp, except that the light must be closer to the tube (5 cm vs. 50 cm for the high-intensity lamp) and the radiation time must be increased to 5–30 sec. This is still very rapid compared to traditional cross-linking techniques.

PICUP should be a useful tool for the analysis of protein-protein contacts in multi-protein complexes. The reaction employs commercially available reagents, is fast, extremely efficient. Using GST as a model substrate, detectable yields (5–10%) of homodimers can be achieved with only a 30 millisecond irradiation using the Xe lamp. It may be possible to reduce this time even further using a laser as the light source. This suggests that the reaction could be very useful for kinetic studies of the dynamics of protein-protein associations. PICUP is the first analytically useful system in which protein cross-linking can be efficiently triggered with visible light. Previous descriptions of crosslinking with visible light has demonstrated only slow, low-level photo-coupling of proteins mediated by protoporphyrin (Verweiji et al., 1981). The use of long-wavelength light is attractive because few biomolecules absorb outside of the UV region, an important point in carrying out cross-linking in crude extracts or eventually in living cells.

EXAMPLE 5

Peptide- or Small Molecule-Metal Ligand Conjugates as Antibody Equivalents

Several genetic selection schemes exist that make it routine to search libraries for peptides that bind protein or peptide targets with remarkable specificity, rivaling that of a good monoclonal antibody. These peptides are potential antibody substitutes, but a problem is that their affinities for the target are modest and must be improved for use in various applications. The present invention using novel photo-activated cross-linking chemistry allows one to trap covalently these moderate affinity interactions. The strategy is to first react the low affinity peptide with a crosslinking reagent such as ruthenium pyridyl or palladium porphyrins creating a novel molecular probe. This probe can then be used to contact a target protein or peptide in the same way as using an antibody to probe for a given target. The solution containing the probe and target protein or peptide would then be exposed to light, trapping the low affinity complex in a stable, covalent complex. The stable, covalent complex could then be detected or isolated by any of a variety of means, making use of the initial molecular probe as an identifying agent. Any methodology dependent on a primary antibody could make use peptide or small molecule conjugates that act like antibodies. Techniques that would be possible to incorporate these conjugates include Western blot applications, ELISAs, inmuunohistochemistry, FACS, and other detection schemes and devices. Synthesizing these small peptide-metal complex conjugates would be orders of magnitude cheaper than making antibodies.

An alternative approach is to use peptide-metal complex conjugates in array technologies. There is a great deal of interest in developing high-density arrays for the detection of protein molecules. This idea would parallel current high-density arrays based on nucleic acid hybridization technologies that probe for nucleic acids. The current rate-limiting step in developing such systems is generation of thousands of specific protein-binding ligands that can be attached in an array. The use of antibodies in such an application is prohibitive. A synthetic or genetic peptide selection system generating large numbers of novel molecules which could then be conjugated with a crosslinking reagent such as ruthenium pyridyl or palladium porphyrins. These could then be used in array technologies to be used as probes for detection of specific proteins, again utilizing cross-linking in the detection scheme.

Figure 6:
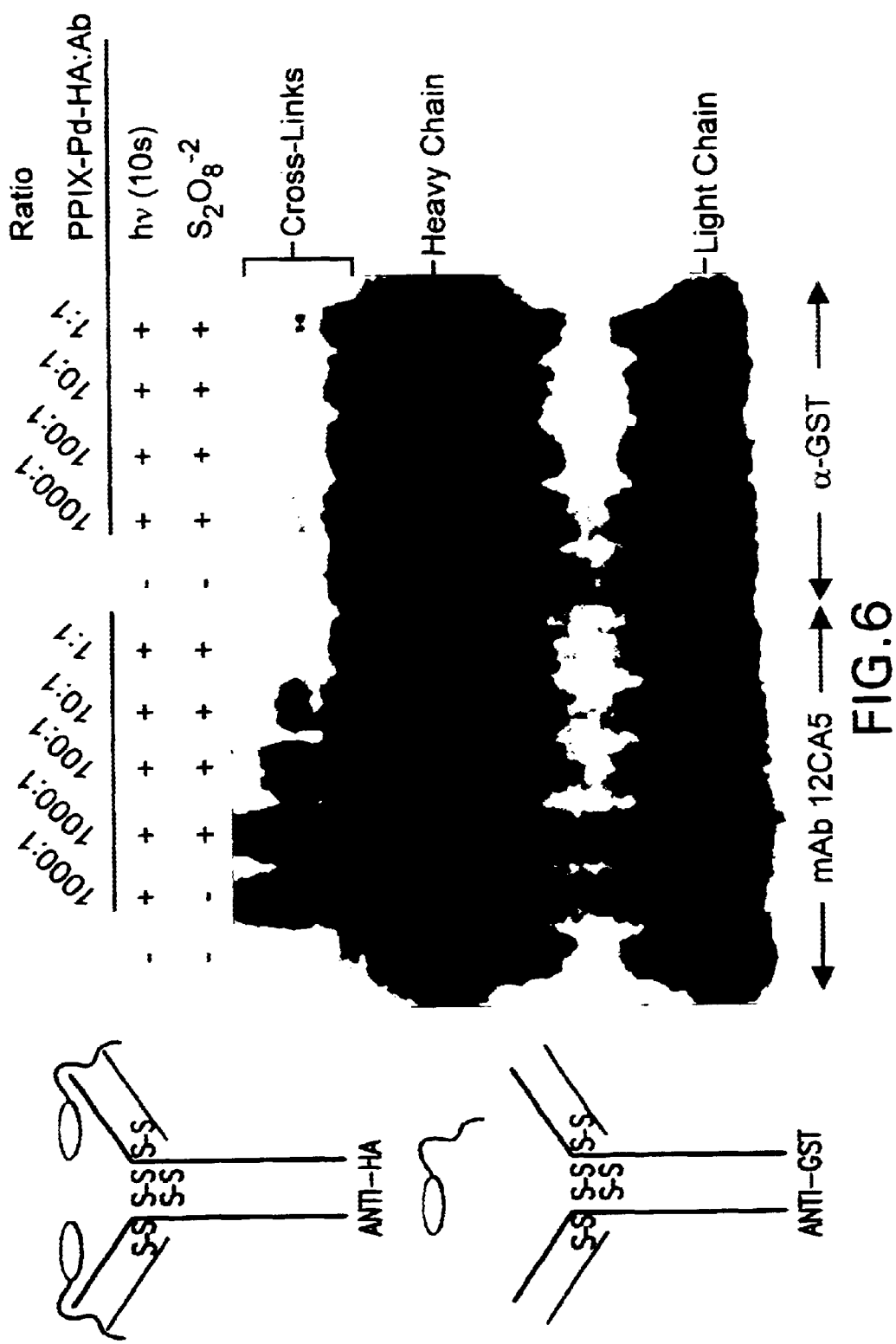
FIG. 6. Western analysis of crosslinked antibody species demonstrates specificity of peptide with antibody. A palladium porphyrin conjugate of a low affinity hemeagglutinin (HA) epitope (PPIX-Pd-HA) was mixed at varios ratios from 1:1 to 1000:1 with either a anti-HA antibody (mAB 12CA5) or a non-specific anti-GST antibody. The mixture was exposed to visible light for 10 seconds in the presence or absence of $S_2O_8^-$. The reaction was stopped by addition of gel running buffer, boiled and seperated by electrophoresis as described in Example 2. Antibody species were detected by Western analysis. Noted on the side of the exposure of the Western analysis are the positions of the antibody light and heavy chains as well as cross-linked antibody species.

FIG. 6. Shows a proof of concept experiment. A peptide was synthesized which resembles the hemeagglutinin (HA) epitope, but which has a single point mutation. This reduces its affinity for the conjugate monoclonal antibody by about 100-fold, placing the $K_D$ of this peptide-protein complex in the range of the peptide-protein complexes that are typically obtained from a genetic selection procedure. A Palladium porphyrin conjugate of the peptide was made, and increasing amounts of this chimera were mixed with the anti-HA antibody and photolyzed for one second with visible light. A control experiment was also conducted using an antibody raised against glutathione-S-transferase (GST), which has a much lower affinity for the HA peptide. Phototrapping was measured indirectly by running the products through a denaturing gel and probing for cross-linked antibody chains. This is a different protocol than one would normally use to detect peptide-protein binding, but served to demonstrate binding and crosslinking in this case. As can be seen in FIG. 6, good yields of cross-linked product were obtained with the anti-HA antibody, with little detectable cross-linked product seen with the anti-GST antibody. This demonstrates that a peptide-protein complex can be phototrapped using our new chemistry, and that much lower levels of phototrapping are observed for mismatched peptide-protein complexes. The inventors are proceeding to make radiolabeled peptide-porphyrin conjugates so that the extent of phototrapping can be measured directly, rather than the indirect way protein-protein crosslinking was measured in this experiment.

EXAMPLE 6

Use of Peptide- or Small Molecule-Metal Ligand Conjugates in Drug Discovery

Several methodologies and screens have been developed for producing small molecule lead compounds, including high-throughput drug screens and combinatorial chemistry approaches. Often times lead compounds interact weakly with the target molecule or the target molecule that a lead compound is interacting with is not well defined. The present invention using novel photo-activated cross-linking chemistry would allow covalent cross-linking of lead compounds with target molecules. The general strategy is demonstrated in FIG. 7. It involves the creation of chimeras of the lead compounds with a cross-linking reagent such as a palladium porphoryn or a ruthenium pyridyl. These chimeras are then exposed to potential target molecules and then photolyzed to couple the lead compound to the target molecule. The newly created complex can then be detected and/or isolated as a way of defining the target molecule. This would help in identifying targets molecules that the lead compounds are interacting with and improve future iterative rounds of lead compound development.

All of the compositions and/or methods disclosed and claimed-herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberts, *Cell* 92:291–294, 1998.

Arap et al., *Cancer Res.*, 55:1351–1354, 1995.

Bass, Greene, Wells, "Hormone phage: an enrichment method for variant proteins with altered binding properties," *Proteins* 8, 309–314, 1990.

Bedzyk et al., *J Biol. Chem.*, 265:18615, 1990

Beemick and Morrical, *Biochemistry*, 37:5673–5681, 1998.

Bertrand, Derancourt, Kassab, *Biochemistry*, 36:9703–9714, 1997.

Blumenroder et al., *Surv. Ophthalmol.* 42:S1 18–26, 1997.

Bolden et al., *J Chromatogr. A.*, 828:421–30, 1988.

Brown, Yu, Burlingame, Craik, *Biochemistry*, 37:4397, 1998.

Browns, Yang, Kodadek, *Biochemistry*, 34:4733–4739, 1995.

Burbage et al., *Leuk Res*, 21(7):681–690, 1997.
Bussemakers et al., *Cancer Res.*, 52:2916–2922, 1992.
Caldas et al., *Nat. Genet.*, 8:27–32, 1994.
Casey et al., *Oncogene*, 6:1791–1797, 1991.
Cech et al., "In vitro splicing of the ribosomal RNA precursor of Tetrahymena: involvement of a guanosine nucleotide in the excision of the intervening sequence," *Cell*, 27:487–496, 1981.
Chaudhary et al. *Proc. Nati. Acad. Sci.*, 87:9491, 1990
Chen, Ebright, Ebright, *Science*, 265:90–92, 1994.
Cheng et al., *CancerRes.*, 54:5547–5551, 1994.
cloned antigens on the surface of the virion," *Science* 228, 1315–1317, 1985.
Coleman, Taggart, Benjamin, Pugh, *J Biol. Chem.*, 270:13842–13849, 1995.
Denison and Kodadek, *Chem. & Biol.*, 5:R129-R145, 1998.
Devlin, Panganiban, Devlin, "Random peptide libraries: a source of specific protein binding molecules," *Science* 249, 404–406, 1990.
Dorman and Prestwich, *Biochemistry* 33:5661–5673, 1994.
Edelman and Crossin, *Annu. Rev. Biochem.*, 60:155–190, 1991.
Edelman, *Annu. Rev. Biochem.*, 54:135–169, 1985.
Fancy and Kodadek, *Tetrahedron*, 53:11953–11960, 1997.
Fancy, Melcher, Johnston, Kodadek, *Chem & Biol.*, 3:551–559, 1996.
Forster and Symons, "Self-cleavage of plus and minus RNAs of a virusoid and a structural model for the active sites," *Cell*, 49:211–220, 1987.
Friedrichson and Kurzchalia, *Nature*, 394:802–805, 1998.
Frixen et al., *J. Cell Biol.*, 113:173–185, 1991.
Gafffey, *Biochim. Biophys. Acta.*, 822:289–317, 1985.
Gerlach et al., "Construction of a plant disease resistance gene from the satellite RNA of tobacco Ringspot virus," *Nature* (London), 328:802–805, 1987.
Giancotti and Ruoslahti, *Cell*, 60:849–859, 1990.
Gill, Richter-Rusli, Ghosh, Burrows, Rokita, *Chem. Res. Tox.*, 10:302–309, 1997.
Gonzalez-Zulueta et al., *Cancer Research*, 55(20):4531–4535, 1995.
Gray and Winkler, *Ann. Rev. Biochen.*, 65:537–561, 1996.
Grimshaw et al., *J. Pharm. Biomed. Anal.* 16:605–12, 1997.
Heinecke, Li, Francis, Goldstein, *Journal of Clinical Investigation*, 91:2866–72, 1993.
Herman et al., *Cancer Research*, 55(20):4525–4530, 1995.
Hogan, *J. Appl. Physiol.* 86:720–4, 1999.
Hollstein et al., *Science*, 253:49–53, 1991.
Hoopes, LeBlanc, Hawley, *J. Biol. Chem.*, 267:11539–11547, 1992.
Hussussian et al., *Nature Genetics*, 15–21, 1994.
Ji, and Ji, *Pharacol Ther.*, 43:321–332, 1989.
Jiang and Kodadek, *J. Biol. Chem.*, 268:7904–7911, 1993.
Jiang, Giedroc, Kodadek, *Biol. Chem.* 268:7904–7911, 1993.
Johnston, *Microbiol. Rev.*, 51:458–476, 1987.
Johnston, Salmeron, Dincher, *Cell*, 50:143–146, 1987.
Joyce, "RNA evolution and the origins of life," *Nature*, 338:217–244, 1989.
Kamb et al., *Nature Genetics*, 8:22–26, 1994.
Kamb et al., *Science*, 2674:436–440, 1994.
Kim and Cech, "Three dimensional model of the active site of the self-splicing rRNA precursor or Tetrahymena," *Proc. Nat'l Acad. Sci. USA*, 84:8788–8792, 1987.
Kodadek, Gan, Stemke-Hale, *J. Biol. Chem.*, 264:16451–16457, 1989.
Lim, Ho, Keeling, Gilliland, Ruker, Carter, *Protein Sci.*, 3:2233–2244.
Lin and Guidotti, *J. Biol. Chem.*, 264:14408–14414, 1989.
Ma and Ptashne, *Cell*, 50:137–142, 1987.
Malencik and Anderson, *Biochemistry*, 35:4375–4386, 1996.
Martsev et al., *J. Immunol. Methods* 186:293–304, 1995.
Massuda et al., *Proc Natl Acad Sci USA*, 94(26):14701–14706, 1997.
Matsura et al., *Brit. J Cancer*, 66:1122–1130, 1992.
Mattson, Conklin, Desai, Nielander, Savage, Morgensen, *Mol. Biol. Rep.* 17:167–183, 1993.
McCafferty, Griffiths, Winter, Chiswell, "Phage antibodies: filamentous phage displaying antibody variable domains," *Nature* 348, 552–554, 1990.
Mel'nikova et al., *Biochemistry* (Mosc) 62:924–7, 1997.
Melcher and Johnston, *Mol. Cell Biol.*, 15:2839–2848, 1995.
Michel and Westhof, "Modeling of the three-dimensional architecture of group I catalytic introns based on comparative sequence analysis," *J. Mol. Biol.*, 216:585–610, 1990.
Milks and Ortiz de Montellano, *J. Biol. Chem.*, 267:8827–8833, 1992.
Mori et al., *Cancer Res.*, 54:3396–3397, 1994.
Needels, Jones, Tate, Heinkel, Kochersperger, Dower, Barrett, Gallop, "Generation and screening of an oligonucleotide-encoded synthetic peptide library," *Proc. Nat'l Acad. Sci. USA* 90, 10700–10704, 1993.
Nickel, Chen, Schneider, Silva, Burrows, Forosinho, *J. Phys. Chem.*, 98:2883–2888, 1994.
Nobori et al., *Nature*, 368:753–756, 1995.
Norcum and Warrington, *Prot. Sci.*, 7:79–87, 1998.
Obrink, *BioEssays*, 13:227–233, 1991.
Odin and Obrink, *Exp. Cell Res.*, 171:1–15, 1987.
Ohlmeyer, Swanson, Dillard, Reader, Asouline, Kobayashi, Wigler, Still, "Complex synthetic chemical libraries indexed with molecular tags," *Proc. Nat'l Acad. Sci. USA* 90, 10922–10926, 1993.
Okamoto et al., *Proc. Nat'l Acad. Sci. USA*, 91:11045–11049, 1994.
Orlow et al., *Cancer Res.*, 54:2848–2851, 1994.
Platt and Reece, *EMBO J.* 17:4086–4091, 1998.
Reinhold-Hurek and Shub, "Self-splicing introns in tRNA genes of widely divergent bacteria," *Nature*, 357:173–176, 1992.
Ridlen et al., *J. Chromatogr. B. Biomed. Sci. Appl.* 694:393–400, 1997.
Sarver, et al, "Ribozymes as potential anti-HIV-1 therapeutic agents," *Science*, 247:1222–1225, 1990.

Scanlon et al., "Ribozyme-mediated cleavages of c-fos MRNA reduce gene expression of DNA synthesis enzymes and metallothionein," *Proc Natl Acad Sci USA*, 88:10591–10595, 1991.

Schere and Krieg, *Methods Cell Biol.*, 34:419–426, 1991.

Scott, Smith, "Searching for peptide ligands with an epitope library," *Science* 249, 386–390, 1990.

Serrano et al., *Nature*, 366:704–707, 1993.

Serrano et al., *Science*, 267:249–252, 1995.

Smith, "Filamentous fision phage: novel expression vectors that display

Stadtman, Free Radical Biology & Medicine, 9:315–325, 1990.

Struhl, *Ann. Rev. Genetics*, 29:651–674, 1995.

Stubbe and Riggs-Gelasco, *Biochem. Sci.*, 23:438–443, 1998.

Takahashi et al., *Cancer Res.*, 52:734–736, 1992.

Tanielian, Wolff, Esch, *J. Phys. Chem.*, 100:6555–6560, 1996.

Tew and Ortiz de Montellano, *J. Biol. Chem.*, 263:17880–17886, 1988.

Torres-Filho et al., *Microvasc. Res.* 51:202–212, 1996.

Umbas et al., *Cancer Res.*, 52:5104–5109, 1992.

Van Hoy, Leuther, Kodadek, Johnston, *Cell* 72:587–594, 1993.

Velasco-Garcia et al., *Analyst.* 122:1405–9, 1997.

Verweij, Dubbelman, Van Steveninck, *Biochemica et Biophysica Acta*, 647:87–94.

Weinberg, *Science*, 254:1138–1145, 1991.

Wherland and Gray, *Proc. Nat'l Acad. Sci USA*, 73:2950–2954, 1976.

Woltman et al., *Anal. Chem.* 71:1504–12, 1999.

Wu, Reece, Ptashne, *EMBO J.*, 15:3951–3963, 1996.

Yocom, Shelton, Shelton, Schroeder, Worosila, Isied, Bordignon, Gray, *Proc. Nat'l Acad. Sci. USA* 79:7052–7055, 1982.

Zhang and Rodgers, *Phys. Chem.*, 99:12797–12803, 1995.

What is claimed is:

1. A method of covalently bonding a first molecule and a second molecule, wherein said first molecule is a protein, comprising:

(i) providing said first protein molecule and said second molecule in proximity to each other;

(ii) contacting said molecules with a metal-ligand complex; and (iii) subjecting said complex to light, whereby said light photoactivates said complex, and said complex causes direct bonding of said first protein molecule to said second molecule without incorporation of the metal-ligand complex.

2. The method of claim 1, wherein said protein is an antibody.

3. The method of claim 1, wherein said protein is a peptide.

4. The method of claim 3, wherein said peptide is conjugated to a metal.

5. The method of claim 1, wherein said second molecule is a protein.

6. The method of claim 1, wherein said complex comprises a detectable agent.

7. The method of claim 1, wherein said complex comprises a palladium(II) porphyrin and an electron acceptor.

8. The method of claim 1, wherein said complex comprises Ruthenium (II)(bypyridyl) and an electron acceptor.

9. The method of claims 7 or 8, wherein said electron acceptor is ammonium persulfate or a cobalt(III) complex.

10. The method of claim 1, wherein said light has a wavelength of >400 nm.

11. The method of claim 1, wherein said first and said second molecules are located in a cell.

12. The method of claim 1, further comprising isolating the complex-linked first and second molecules.

13. The method of claim 12, further comprising identifying said first molecule.

14. The method of claim 12, further comprising identifying said second molecule.

\* \* \* \* \*